(12) United States Patent
Zieris et al.

(10) Patent No.: US 9,585,673 B2
(45) Date of Patent: Mar. 7, 2017

(54) SURGICAL CLIP, IN PARTICULAR ANEURYSM CLIP

(71) Applicant: Aesculap AG, Tuttlingen (DE)

(72) Inventors: Gerold Zieris, Mühlheim (DE); Corvin Motz, Pfullendorf (DE); Joachim Amann, Mühlingen-Zoznegg (DE)

(73) Assignee: Aesculap AG (DE)

( * ) Notice: Subject to any disclaimer, the term of this patent is extended or adjusted under 35 U.S.C. 154(b) by 0 days.

(21) Appl. No.: 14/905,918

(22) PCT Filed: Jul. 8, 2014

(86) PCT No.: PCT/EP2014/064610
§ 371 (c)(1),
(2) Date: Jan. 18, 2016

(87) PCT Pub. No.: WO2015/010893
PCT Pub. Date: Jan. 29, 2015

(65) Prior Publication Data
US 2016/0157867 A1    Jun. 9, 2016

(30) Foreign Application Priority Data
Jul. 23, 2013  (DE) .................. 10 2013 107 876

(51) Int. Cl.
*A61B 17/122* (2006.01)
*A61B 17/00* (2006.01)

(52) U.S. Cl.
CPC *A61B 17/1227* (2013.01); *A61B 2017/00685* (2013.01)

(58) Field of Classification Search
CPC .................. A61B 17/1227; A61B 2017/00685
USPC .................. 606/157, 158, 205, 207
See application file for complete search history.

(56) References Cited

U.S. PATENT DOCUMENTS

| | | | |
|---|---|---|---|
| 4,932,955 A | 6/1990 | Merz | |
| 7,874,343 B2* | 1/2011 | Hansen | B60J 1/2027 160/299 |
| 2004/0092961 A1 | 5/2004 | Viola | |
| 2006/0195125 A1 | 8/2006 | Sakakine | |
| 2015/0008629 A1* | 1/2015 | Kuno | F16F 1/10 267/156 |

FOREIGN PATENT DOCUMENTS

| | | |
|---|---|---|
| DE | 3523031 | 1/1986 |
| DE | 20303496 | 7/2003 |

(Continued)

OTHER PUBLICATIONS

"Motives Definitions, Requirements, Testing", DiN 8287, Apr. 1983, pp. 1-5, with English language translation.

(Continued)

*Primary Examiner* — Vy Bui
(74) *Attorney, Agent, or Firm* — RatnerPrestia

(57) ABSTRACT

A surgical clip includes a first clamping arm and a second clamping arm rotatably coupled to each other and pre-stressed against each other into a closed position by a spring in the rotational direction, a first housing part being formed or arranged on the first clamping arm and a second housing part being formed or arranged on the second clamping arm, the housing parts forming a housing in which the spring is received.

12 Claims, 3 Drawing Sheets

(56) References Cited

FOREIGN PATENT DOCUMENTS

Figure 1:
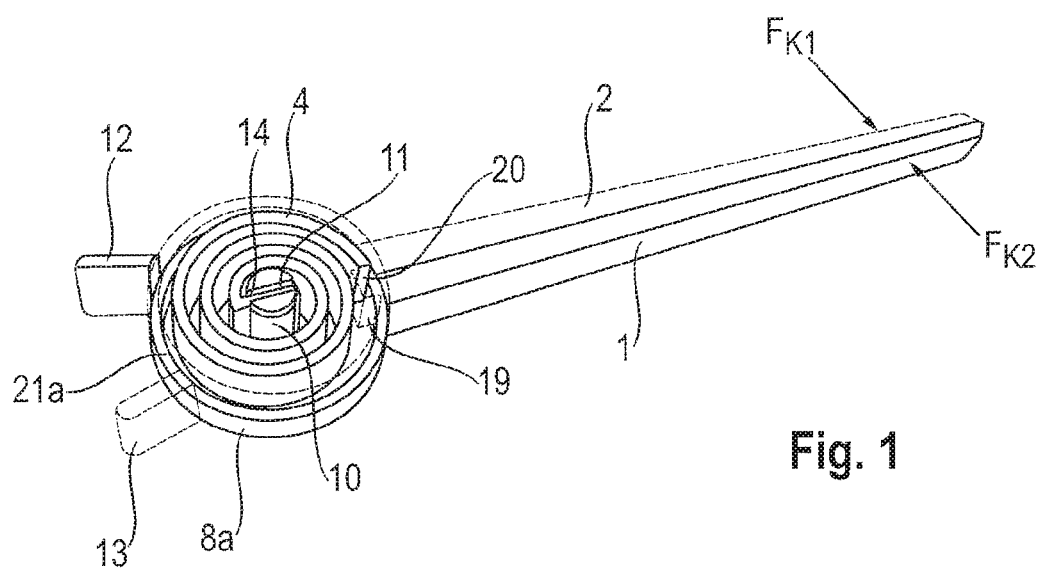

| DE | 10309491 | 9/2004 | | |
|---|---|---|---|---|
| DE | 202011051881 | 11/2011 | | |
| DE | 102011055094 | 5/2013 | | |
| EP | 2589346 | 5/2013 | | |
| GB | 2161206 | 1/1986 | | |
| JP | S6124807 | 2/1986 | | |
| JP | 2006519674 | 8/2006 | | |
| WO | 2004080275 | 9/2004 | | |
| WO | WO 2013/111416 A1 * | 8/2013 | ................ | F16F 1/10 |

OTHER PUBLICATIONS

German Office Action for German Application No. 10 2013 107 876.1 mailed Jul. 8, 2015, including English translation.
International Search Report for International Application No. PCT/EP2014/064610 mailed Oct. 13, 2014.
Kunne, et al. "Machine Parts 1" 10th Edition, Bibliographic Information of the German National Library, ISBN 978-3-83-51-0093-0, pp. 1-4, with English language translation.
Written Opinion of the International Search Authority for PCT/EP2014/064610 mailed Oct. 13, 2014.
Chinese Office Action dated Jul. 21, 2016 for Chinese Application No. 201480041783.6, including translation, 12 pages.
Japanese Office Action for Japanese Application No. 2016-517380, dated Jun. 28, 2016, with translation, 4 pages.
Japanese Office Action for Japanese Application No. 2016-517380, mailed Nov. 29, 2016, including English translation, 4 pages.

* cited by examiner

SURGICAL CLIP, IN PARTICULAR ANEURYSM CLIP

RELATED APPLICATION(S)

This application is the United States national phase entry of International Application No. PCT/EP2014/064610, filed Jul. 8, 2014, which claims the benefit of priority of German Application No. DE 10 2013 107 876.1, filed Jul. 23, 2013. The contents of International Application No. PCT/EP2014/064610 and German Application No. DE 10 2013 107 876.1 are incorporated by reference herein for all purposes.

FIELD

The present invention relates to a surgical clip, in particular an aneurysm clip, comprising a first clamping arm or jaw part and a second clamping arm or jaw part which are rotatably coupled to each other by means of a hinge and are prestressed against each other into a closed position by means of a spring in the rotational direction.

BACKGROUND

Surgical clips are medical instruments or implants which are temporarily used for pinching off or closing tissue perforations or are employed as vessel clamps for a medical long-term care for e.g. aneurysms. A multitude of different clips is known, for instance in the form of jaw-like clips in which the clamp or clip branches are formed to be curved in longitudinal direction similar to the upper and lower jaw and are coupled to each other at their two ends via a hinge.

Another example is represented by slim, elongated clips similar to conventional pliers, comprising two opposite clamping arms (branches) which are provided with teeth or a fluting and have their ends coupled to each other in the manner of a hinge.

The clips according to the prior art usually have two jaw parts coupled to each other in hinge-like fashion, said jaw parts each forming a clamping portion (in the following also referred to as a clamping arm or branch) and an operating portion. Further, the clips basically comprise a spring assembly which serves for preloading the clip into its closed position and brings about a clamping force which is exerted by the clip branches or clamping arms. There are clips in which the spring assembly is a separate component cooperating with the jaw parts of the clip, as well as clips in which the spring assembly is an integral component of the clip or of the jaw parts.

Aneurysm clips are known in which the branches or clamping arms are preloaded against each other by means of a U-shaped leg spring. The legs of such a leg spring either engage the clamping arms directly from outside or laterally and compress them, or they engage operating portions each prolonging the clamping arms in the longitudinal direction of the clip and compress them or pull them apart, depending on whether the jaw parts intersect or are parallel in the hinge area.

However, the use of a leg spring results in some disadvantages. Leg springs, in particular those comprising an energy storage means which is wound in spiral shape, usually require a comparably expensive and complex manufacture. In particular during the winding process, it has to be ensured that there is no cracking in the spring material. An excessive level of winding the leg spring is to be avoided, too, as otherwise the pressing force between the clamping arms may be reduced. All in all, the manufacture of leg springs requires a high level of precision in order to manufacture instruments whose attributes such as pressing force, durability, operational safety etc. are within a narrow range of tolerance.

A further problem in using leg springs is the provision of a reproducible pretensioning force. The leg spring has to be designed and dimensioned such that a predetermined pretensioning force is acted upon the clamping portions. This is decisive for the achievable maximum closing force. With predefined dimensions of the clip, it may be problematic to achieve the desired closing force which can be obtained at least a lot of times only with high efforts. It may also happen that there is a plastic deformation of the spring area, in particular in the case of a low number of windings or with a pure U-shape of the leg spring, with the number of windings ranging between 0.5 and 2 depending on the available installation space.

As a leg spring is usually arranged so as to be asymmetric relative to the branches of the clip or to its clamping arms, it may disadvantageously happen that frictional forces occur between the branches or clamping arms and the legs of the spring which cooperate with them. This results in a reduction of the maximum achievable closing force. In addition, the asymmetric arrangement may have the effect that the clamping arms of the clip do not open and close in parallel fashion. A further disadvantage is that there usually is only a linear contact between the legs of the spring and the branches.

From DE 10 2011 055 094 A1 an aneurysm clip is known which comprises a first jaw part including a clamping arm, a fork portion being formed on one proximal end region of said clamping arm. The clip further comprises a second jaw part comprising a clamping arm on whose proximal end a spiral spring is formed. The latter is inserted in the fork portion of the first jaw part and guided therein in such a manner that it is coupled to the fork portion in a torque-proof manner. This usage of a spiral spring avoids some of the afore-mentioned disadvantages of leg springs. However, the leg spring comes into contact with body tissue with this sort of clip as well as with the previously described clips, so that the material of the spring has to meet the same demands with respect to body compatibility and hygiene than the material of the jaw parts.

SUMMARY

Starting from the previously described prior art, the invention is based on the object to provide a surgical clip, in particular an aneurysm clip with an especially slim design, which can be easily applied with smallest possible limitations, has a good handling and can be easily cleaned. One object is to provide a surgical clip (an aneurysm clip) with which the achievement of a defined pretensioning force is ensured. Further, it would be advantageous if plastic deformations of the spring or partial zones of the spring can be avoided and a defined opening and closing of the clamping arms is possible without canting and asymmetry.

In particular, a surgical clip (aneurysm clip) is provided according to the invention, comprising a first and a second jaw part which are rotatably coupled to each other, in particular by means of a hinge, and which are preloaded against each other in the rotational direction into a closed position of the clip by means of a spring, wherein a first housing part is formed or arranged on the first clamping arm and a second housing part is formed or arranged on the second clamping arm, said housing parts cooperating for the formation of a housing which is essentially closed towards outside and in which the spring is received.

Each jaw part of the clip preferably has a clamping arm portion or branch each being formed in a (distal) portion preferably in a shell-like manner into a housing part. According to one embodiment, the first housing part and/or the second housing part may be formed from a cylinder-shaped wall comprising a closed end face each (i.e. like a cup). The housing parts of the clamping arms or of the two jaw parts match each other and fit into each other and form the housing in which the spring is internally arranged. Specifically, the housing portions and hence the entire housing as well as the spring may be formed to be symmetric to a plane extending transversely to the rotational axis of the clip, so that the loading of the spring occurs only transverse to the rotational axis and a symmetric introduction of spring forces into the branches is ensured without any transverse force components in the direction of the rotational axis of the clip.

Advantageously, the spring is protected in the housing against the surroundings. Thus, there is no need that the spring material meets the same demands as the material of the jaw parts or of the housing; rather, it can be selected and used with a specific view on optimized spring characteristics. It is a special benefit that the spring is protected in the housing. In this way, it is possible to effectively avoid any damage of the spring. Only the two clamping arms of the clip, possibly the two operating portions adjoining the housing parts in proximal extension of the clamping arms, as well as the outer side of the housing encasing the spring are visible from outside or point outward. In this way, it is particularly simple to form smooth surfaces without any depressions, edges, undercuts or the like where contaminations may accumulate. Moreover, a clip comprising a simple, largely smooth external configuration can be easily applied.

With a first spring end region, the spring can be arranged in the housing in a torque-proof manner on one of the two clamping arms/jaw parts and preferably be retained there. With the opposite spring end region, the spring is (loosely) supported on the other clamping arm/jaw part within the housing; by way of example, it rests against a protrusion or is received in a recess. When assembling the two jaw parts (or jaw part halves), the spring (firmly) retained in/on one of the two jaw parts is prestressed up to the preload which is required for achieving the desired clamping force, in particular by bringing the other spring end, with elastic deformation of the spring, in operative engagement with the protrusion/recess of the other jaw part. In this way, a simple assembly of the clip is made possible with benefit without mandatory use of additional tools. What is more, the desired clamping force of the clip can be achieved by a suitable selection of the spring or by varying the preload e.g. by correspondingly arranging spring-supporting elements (protrusion, recess, etc.); in particular, said clamping force is easy to reproduce.

According to one embodiment, the first housing part may be formed or arranged on the end side of the first clamping arm and/or the second housing part may be formed or arranged on the end side of the second clamping arm. This allows to realize a slim, elongated clip which takes up a particularly small space and can be easily handled in confined conditions. Preferably, both housing portions are arranged so as to be aligned with the clamping arms of the branches.

In one embodiment, the clip may comprise an axle pin which is formed or arranged in the interior of the housing. It may be fixedly arranged on one of the two housing parts or may be formed in one piece with it, while it engages a corresponding seating (hole) of the other housing part.

Advantageously, the axle pin is able to serve several purposes. On the one hand, it is capable of mutually centering the two jaw parts or clamping arms and holding them. On the other hand, it can define the rotational axis of the hinge. According to a further development of the invention, it finally can bring about a (possibly) torque-proof fixation of the (spiral) spring. To this aim, the axle pin may comprise a seating preferably in the form of a recess or of a slot. Advantageously, an end portion of the spring is received and retained in said recess or slot. According to one embodiment of the invention, the axle pin is rotationally fixed relative to one of the two housing portions and is rotatable relative to the other one of the two housing portions with respect to the rotational axis of the hinge.

As an alternative or in addition to the axle pin, the hinge of the clip may be defined by the housing wall or by portions of the housing wall itself. Therefore, according to one embodiment, the cylinder-shaped walls of the first housing part and of the second housing part each comprise support areas or support portions which engage into each other or cooperate and define the hinge.

The clip may have its operating portions or operating elements realized for instance in the form of lugs, protrusions or the like. These may serve, among other things, for opening the clip against the preload of the spring and are arranged or formed preferably on the first housing part and/or on the second housing part. Moreover, the operating elements may be formed such that they define and delimit the maximum opening angle of the clip. In this way, any overstretching of the spring is advantageously prevented, so that a premature fatigue of the spring can be largely avoided and the achievement of the desired closing force is ensured even after an extended period of use.

According to a particularly advantageous embodiment of the invention, the spring is a spiral spring. This guarantees a comparably large spring deflection also with small outer dimensions of the spring, so that the clip can be opened to a large degree without plastically overbending the spring or breaking it. Particularly preferred is a spiral spring in the form of a flat spiral, which can be arranged exceptionally well in symmetric way to the clamping arms of the clip and in particular so as to be aligned in their longitudinal direction. This has the effect that the clamping arms open and close in an essentially parallel manner.

With particular benefit, the spring has the shape of an Archimedean spiral, so that there is a constant clearance between active windings of the spring. The housing made up of the first and the second housing portions advantageously forms a lateral, preferably double-sided guide for the spring. When the clip is opened or closed, accompanied by an elastic deformation of the spiral spring, i.e. an expansion or contraction, the spring cannot bulge out sideward or cant, counteracting a premature fatigue of the material.

According to a further embodiment of the invention, the spring may comprise a rectangular cross-section, ensuring a defined direction of the pretensioning force caused by the spring and proving to be advantageous for a parallel opening and closing of the clamping arms of the clip. The rectangular cross-section of the spring also counteracts a lateral bulging of the spring when under bending stress. Finally, a spiral spring comprising a rectangular spring cross-section can be manufactured in a particular simple way in one operation, for instance by laser cutting or by stamping, so that the desired characteristics of the spring (and those of the clip which are dictated by them such as e.g. a defined reproducible pretensioning force) can be provided in a simple, reliable and precise manner.

Preferably, the spiral spring has 1.5 to 3 windings in order to reliably ensure a sufficient opening angle for the two branches or clamping arms (or clamping rails). As the spiral spring, as has been indicated above, can be manufactured by an automatic, possibly material-removing manufacturing process such as cutting, stamping etc., small manufacturing tolerances can be realized with a low reject rate, which renders the clip low-cost as a whole, increases the quantities and enhances the operational safety.

All in all, a clip according to the present invention offers a large spring force while having small space requirements, rendering it universal and usable in wide fields of surgical applications. Compared to a clip according to the prior art, a significantly smaller installation space is needed. Furthermore, the surface area via which the spring is supported on the jaw parts/clamping arms, can be much larger with the invention than in case of using a leg spring.

The invention offers the possibility that the spring and the jaw parts (in particular the clamping arms or branches) can be made of different materials. By way of example, the jaw parts/clamping arms may be made from plastics or ceramics and can be manufactured in particular by means of injection molding methods or with similar techniques. In this way, it is also possible to produce clamping arms with complex geometries, e.g. bayonet or window, in a simple and low-cost manner. It is also possible to get clips which avoid artefacts in the course of CT or MRT procedures. Regarding the spring, however, it is possible to select the materials which are optimal with respect to the spring characteristics.

BRIEF DESCRIPTION OF THE DRAWING FIGURES

Figure 2:
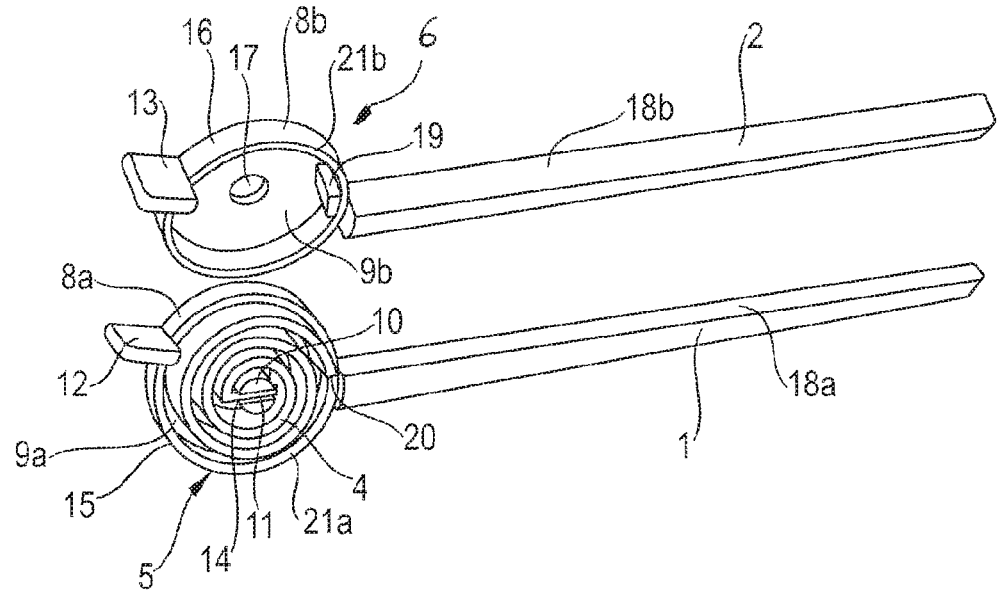
Figure 3A:
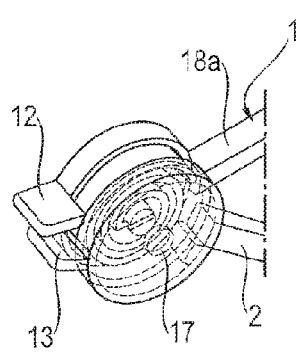
Figure 3B:
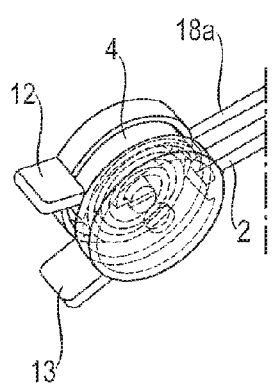
Figure 3C:
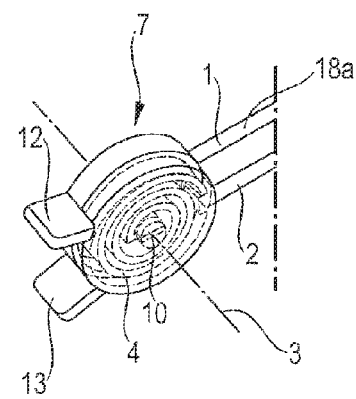

Further features and advantages of the present invention will be apparent from the following exemplary description of a particularly preferred embodiment of the invention on the basis of the Figures in which:

FIG. 1 shows an embodiment of a surgical clip according to the invention in a perspective, partially sectioned view, FIG. 2 shows an embodiment of a surgical clip according to the invention in a perspective view and a partially dismantled state and FIGS. 3a, 3b and 3c show the clip of FIG. 2 in three perspective partial views in different mounting states.

DETAILED DESCRIPTION

The surgical clip shown in FIGS. 1 and 2 is represented in a partially sectioned or partially dismantled illustration. Accordingly, the clip comprises two jaw parts (jaw part halves), i.e. a first jaw part 15 comprising a first clamping arm (or branch) 1 and a second jaw part 16 comprising a second clamping arm (or branch) 2. The two jaw parts 15 and 16 and hence the clamping arm 1 and the clamping arm 2 are coupled to each other in a rotatable or pivotable fashion and are preloaded against each other in a rotational direction toward a closed clip position by means of a spring 4. The clip in FIG. 1 as well as in FIG. 3c is shown in said position in which the clamping arms 1 and 2 are pressed against each other with a desired clamping force. The clamping force acting between the clamping arms 1 and 2 is indicated in FIG. 1 with arrows $F_{K1}$ and $F_{K2}$. The clamping arms 1 and 2 are each elongated and comprise flat clamping surfaces 18a, b that face each other in the assembled state—which is illustrated in FIGS. 1 and 3c—and taper toward their respective free (distal) ends (in FIG. 1 toward the left). In the illustrated embodiment, the clamping surfaces 18a, b are formed to be smooth, but they may also be provided with a suitable profiling, for instance a toothed or grooved structure.

The first jaw part 15 comprises a first housing portion or housing part 5 which is formed or arranged on the proximal end of the first clamping arm 1. The second jaw part 16 comprises a second housing portion or housing part 6 which is formed or arranged on the proximal end of the second clamping arm 2. FIG. 1 shows the housing portion 6 of the second jaw part 16 in a cutaway view only in a schematic manner. In FIGS. 3a to 3c, the housing portion 6 is illustrated in transparent fashion to make clear the position and arrangement of any units of the clip which are concealed by the housing portion 6.

As already indicated above, the housing portions 5 and 6 are formed or arranged on the respective clamping arm 1 or 2 at the end side opposite the free (distal) end of the clamping arm 1 or 2. They form a housing 7 when the jaw parts 15 and 16 are assembled, as is illustrated in FIGS. 1 and 3c. In the illustrated embodiment, said housing is substantially closed against the surroundings. The spring 4 is accommodated in the housing 7.

Both the first housing portion 5 and the second housing portion 6 are realized in the form of a closed hollow cylinder each comprising a cylinder-shaped wall 8a, b and an essentially closed end face 9a, b. An axle pin 10 is arranged or formed in the center of the one end face 9a of the first housing portion 5 of the first jaw part 15 and projects towards inside into the housing 7. An opening (a hole) 17 is formed in the center of the end face 9b of the housing portion 6 of the second jaw part 16 so as to be opposite the axle pin 10 and matching it. Having assembled the jaw part 15 with the jaw part 16 (see FIGS. 1 and 3c), the axle pin 10 engages the opening 17 and is guided therein so as to be rotatable around its longitudinal axis. In the illustrated embodiment, the longitudinal axis of the axle pin 10 defines a rotational axis 3 of the clip around which the two jaw parts 15 and 16 can pivot relative to each other.

The inner side of the cylinder-shaped wall 8a of the first housing portion 5 is formed to be smooth in the circumferential direction on its side facing the axle pin 10. A protrusion 19 is formed on the inner side of the cylinder-shaped wall 8b of the second housing portion 6 facing the axle pin 10. The latter projects from the inner side of the wall 8b into the interior of the housing portion 6 and hence of the housing 7 and extends beyond the height of the wall 8b in orthogonal direction related to the end face 9b of the housing portion 6. The height of the protrusion 19 is dimensioned such that its portion protruding over the wall 8b of the second housing portion 6 is as large as or slightly smaller than the height of the wall 8a of the first housing portion 5 as measured on its inner side, so that the protrusion 19 extends substantially over the entire internal height of the housing 7 when the jaw parts 15, 16 are assembled.

The axle pin 10 comprises a slot 11. Said slot is formed to be continuous in the longitudinal direction of the axle pin 10, i.e. in the direction of the rotational axis 3 of the clip, and serves as a seating for the spring 4. An end portion 14 of the spring 4 is inserted in the slot 11 and held therein at least in torque-proof manner, so that the end portion 14 is connected to the first jaw part 15 in a torque-proof fashion. With respect to the two housing halves or housing portions 15 and 16, the length of the axle pin 10 is dimensioned such that its free end protrudes into the opening 17 when the jaw parts 15, 16 are completely assembled. The diameters of the axle pin 10 and the opening 17 are formed such that the axle pin 10 is rotatably guided therein. The protrusion 19 on the housing portion 6 forms a stop for the free end 20 of the spring 4 opposite the end portion 14.

On the side of the housing portion 5 radially opposite the clamping arm 1, there is formed an operating protrusion 12 which extends, as it were, in (angular) prolongation to the clamping arm 1 and protrudes radially outward from the outer side of the wall 8a. On the side of the housing portion 6 radially opposite the clamping arm 2, an operating protrusion 13 is formed in a corresponding manner, radially protruding towards outside from the outer side of the wall 8b. The operating protrusions 12, 13 define attachments or keys by means of which the clip can be manually opened against the tension of the spring 4. Due to their respectively angled orientation relative to the associated clamping arm, they also limit the maximum opening width of the clip, so that an overtwisting of the spring 4 is prevented and a sufficiently long service life of the spring 4 is ensured.

In the illustrated embodiment, the two jaw parts 15, 16 of the clip intersect in scissor-like manner, so that the process of opening the clip is performed by moving the protrusions 12 and 13 away from each other or pushing them apart. In another embodiment which is not illustrated in the Figures, the jaw parts 15, 16 do not cross each other, but extend one beside the other. In this case, opening the clip is performed by moving the protrusions 12 and 13 toward each other or compressing them. The two afore-mentioned embodiments differ by the winding direction of the spring 4.

In the embodiments illustrated in the Figures, the spring 4 is embodied in the form of an Archimedean spiral having a constant clearance between the active windings. It consists of a flat band with rectangular cross-section. The width of the spring 4 is equal to or slightly smaller than the internal height of the housing 7, so that it is guided and supported on both sides on the end face 9a, b. The free end 20 of the spring 4 has its end face making a full-surface contact on the protrusion 19, so that an optimum support of the spring 4 on the largest possible area is achieved. The end face of the free end 20 of the spring 4 is formed to be orthogonal with respect to its winding direction. The area of the protrusion 19 where the free end 20 is supported is formed in a corresponding manner. Guiding the spring 4 by means of its end portion 14 is also performed orthogonal to the winding direction, so that the introduction of any transverse force components into the spring 4 is avoided when the spring 4 is tensioned during opening the clip, the spring being stressed purely in the direction of the windings (in expanding direction). The spring 4 is symmetrically formed and arranged in the clip, in particular is formed and arranged to be symmetrical to the middle axis of the clamping arms 1 and 2 extending in the longitudinal direction of the clamping arms 1 and 2. This ensures a symmetrical loading and deformation of the spring 4 transverse to the rotational axis 3 of the clip or of the jaw parts 15, 16 coupled to each other in hinge-like fashion, as well as a symmetrical load on the jaw parts 15 and 16 by the spring force. Any canting of the jaw parts 15 and 16 and hence of the clamping arms 1 and 2 including their clamping surfaces 18a, b is not possible and it is ensured that the intended clamping forces are safely applied in extensive zones and the clamping arms 1 and 2 open in parallel manner.

Due to the previously described configuration of the clip, the latter can be assembled in an easy way and without using additional tools. The FIGS. 3a, 3b and 3c schematically show different stages of assembling the two jaw parts 15 and 16. In the stage shown in FIG. 3a, the spring 4 is placed in the first housing portion 5 of the first jaw part 15. In doing so, its end portion 14 is received in the slot 11 of the axle pin 10, so that the spring 4 is protected from being rotated with respect to the first jaw part 15.

The second jaw part 16 is loosely laid on the first jaw part 15, the spring 4 being arranged in the associated housing half. In doing so, the jaw parts 15 and 16 are spaced from each other in the direction of the rotational axis 3. The clamping arms 1 and 2 are offset so as to be rotated around the future pivot axis and can be moved from the position illustrated in FIG. 3a—in which the jaw parts do not cross each other but extend parallel to each other—to the positions illustrated in FIGS. 3b and 3c in which the jaw parts cross each other in a scissor-like manner. During said rotary movement of the jaw parts 15 and 16 into the crossing arrangement, the clamping arms 1 and 2 are swiveled about the rotational axis 3 and moved past each other. While the distance of the jaw parts 15 and 16 in the direction of the future rotational axis 3 of the clip allows the previously described movement of the clamping arms 1 and 2 past each other, the free end 20 of the spring 4 is already in partial engagement with the protrusion 19. In the course of the previously described process of rotating the two jaw parts 15 and 16 relative to each other, the pretensioning of the spring 4 is performed, too.

The strength of the spring 4 as well as the orientation of the slot 11 of the axle pin 10 and of the protrusion 19 relative to each other define the preload of the spring 4. The desired preload of the spring 4 is achieved as soon as the jaw parts 15 and 16 have been moved from the position shown in FIG. 3a to the position shown in FIG. 3b in which the clamping arms 1 and 2 have just been moved to be completely one above the other and do not overlay each other any longer. Starting from this position, the completion of the assembly of the jaw part 15 and 16 is performed by pushing them together in the direction of the future rotational axis 3, here in the direction of the axle pin 10, until the clamping surfaces 18a, b of the two clamping arms 1 and 2 make a full-surface contact on top of each other. In this position, the jaw parts 15 and 16 are also guided relative to each other in axial direction. In this position, i.e. when assembling the jaw parts 15 and 16 has been finished, the end faces 21a, b of the cylinder-shaped walls 8a, b rest against each other, so that the housing 7 enclosing the spring 4 is (substantially) closed. The spring 4 is fully protected by the housing 7 and any inadvertent damaging cannot occur. The clip comprises an essentially closed, smooth external surface, simplifying the application of the clip as well as its cleaning.

In the illustrated embodiments, the spring 4 on the one hand and the jaw parts 15 and 16 on the other hand may consist of different materials. By way of example, the jaw parts 15 and 16 are made of plastic or ceramics and are produced by means of injection molding, whereas the spring 4 consists of a common spring steel.

The invention claimed is:

1. A surgical clip comprising a first clamping arm and a second clamping arm, the first clamping arm and the second clamping arm rotatably coupled with each other relative to a rotational axis and pre-tensioned against each other into a closed position in a rotational direction by a spring, wherein
   a first housing part is formed or arranged on the first clamping arm, and a second housing part is formed or arranged on the second clamping arm, said housing parts cooperating to form a housing in which the spring is held, wherein the spring is a spiral spring in the form of a level spring, the surgical clip comprising an axle pin which is centrally formed or arranged in the interior of the housing, the axle pin comprising a seating in the form of a recess or a slot in which an end section of the spring is held, the axle pin being, rotationally fixed relative to one of the two housing parts and rotatable relative to the other one of the two housing parts with respect to the rotational axis.

2. The surgical dip according to claim 1, wherein the first housing part is formed or arranged on the first clamping arm at a proximal end side and/or the second housing part is formed or arranged at a proximal end side on the second clamping arm.

3. The surgical clip according to claim 1, wherein the first housing part and/or the second housing part is/are formed by a cylinder-shaped wall comprising a closed facing side.

4. The surgical clip according to claim 3, wherein the cylinder-shaped wall of the first housing part and of the second housing part each comprise support areas or support portions which engage each other or cooperate to form a hinge via which the first clamping arm and the second clamping arm are rotatably coupled to each other.

5. The surgical clip according to claim 1, wherein the axle pin forms the rotational axis of a hinge by which the first clamping arm and the second clamping arm are rotatably coupled with each other.

6. The surgical clip according to claim 1 comprising operating elements which serve for opening the clip against the preload of the spring and are formed or arranged on the first housing part and/or the second housing part.

7. The surgical clip according to claim 6, wherein the operating elements define a maximum opening angle of the clip.

8. The surgical clip according to claim 1, wherein the spring is in the form of an Archimedean spiral.

9. The surgical clip according to claim 1, wherein the spring has a rectangular cross-section.

10. The surgical clip according to claim 1, wherein the other of the two housing parts comprises a protrusion, and the spring comprises a free end opposite the end section held in the seating, the protrusion forming a stop for the free end of the spring.

11. The surgical dip according to claim 10, wherein the free end of the spring comprises an end face that is orthogonal to a winding direction of the spring, the end face making a full-surface contact on the protrusion so that the spring is guided by the protrusion in a direction orthogonal to the winding direction to avoid introduction of transverse force components into the spring.

12. The surgical clip according to claim 1, wherein the end section of the spring held in the seating passes through the rotational axis.

* * * * *